(12) United States Patent
Pittman et al.

(10) Patent No.: US 6,310,345 B1
(45) Date of Patent: Oct. 30, 2001

(54) POLARIZATION-RESOLVING INFRARED IMAGER

(75) Inventors: William C. Pittman; Richard G. Westrich; Huey F. Anderson, all of Huntsville, AL (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/415,255

(22) Filed: Oct. 12, 1999

(51) Int. Cl.⁷ .......................... H01L 31/00; G02B 26/10; G01J 5/00
(52) U.S. Cl. .................. 250/334; 250/330; 250/335.1
(58) Field of Search ................................ 250/334, 330, 250/332, 336.1, 338.1, 339.01

(56) References Cited

U.S. PATENT DOCUMENTS 5,369,276 * 11/1994 Antesberger ..................... 250/334

OTHER PUBLICATIONS

An article entitled "Infrared Polarimetric Sensors for Missile Weapon Systems" by Huey F. Anderson, presented at the "Workshop on Infrared and Millimeter Wave Polarimetry" and published in Apr. 1996 in the proceedings as Special Report RD–MG–96–8. This article was also made releasable to the NATO.

* cited by examiner

Primary Examiner—Hung Xuan Dang
(74) Attorney, Agent, or Firm—Arthur H. Tischer; Freddie M. Bush; Hay Kyung Chang

(57) ABSTRACT

The polarization-resolving infrared imager employs the configurations of either first-generation (60 horizontal rows by 1 vertical column of detector elements (pixels)) or second-generation (at least 240 horizontal rows by 4 vertical columns of detector elements (pixels)) infrared imaging detector devices and polarization filters that work in conjunction with the infrared imaging detector devices to separate incoming infrared radiation into portions each having a different polarization orientation. Such polarization separation enables the production of visible images in which various aspects of the scene are differentiated. In the preferred embodiment using the second-generation infrared imaging detector device, polarization-filtering grids are integrated onto the detector. The detector elements in three of the four columns have coupled thereto polarization filtering elements to filter, respectively, horizontal, vertical and 45-degree polarizations of the incoming infrared radiation. Using a scan mirror of sufficient sweep in conjunction with the detector device and the polarization-filtering grid results in one frame of the scene with horizontal polarization, one frame with vertical polarization, one frame with 45-degree polarization and a frame with no polarization distinction, all with one sweep of the scan mirror in real-time scenario. This provides nearly simultaneous infrared scenes at different polarizations from a single cycle of the scan mirror.

11 Claims, 5 Drawing Sheets

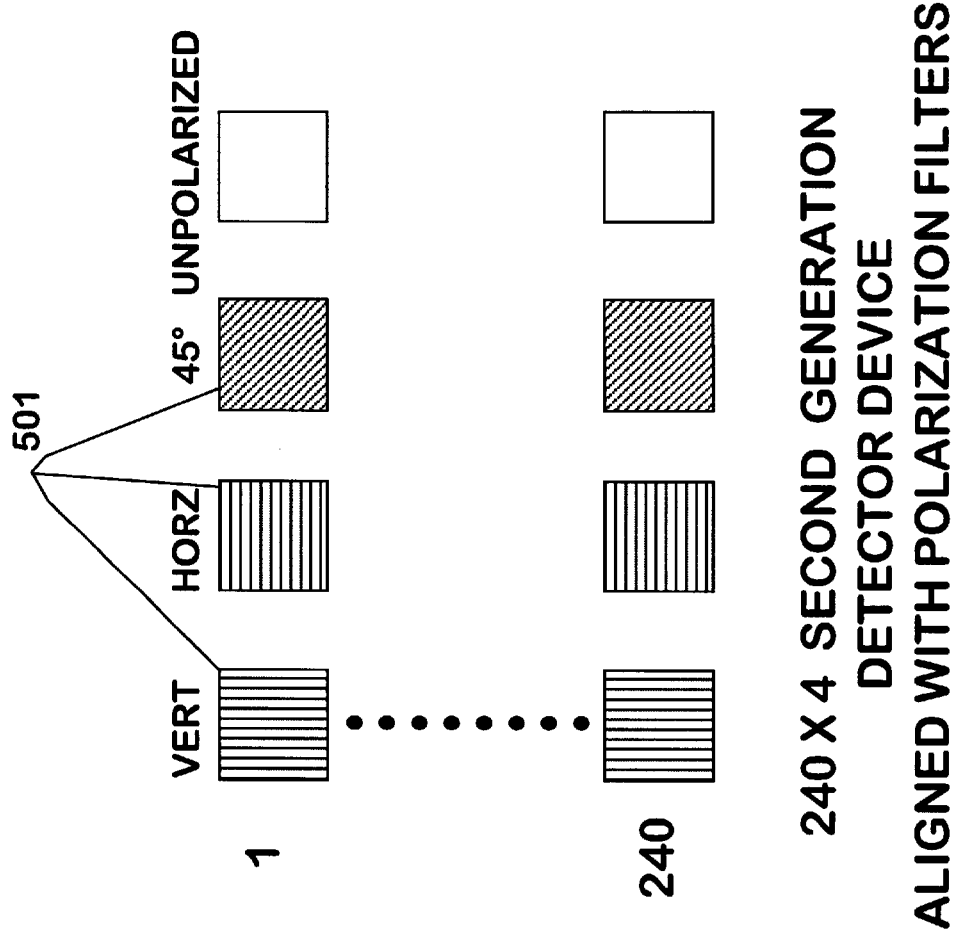

POLARIZATION-RESOLVING INFRARED IMAGER

The invention described herein may be manufactured, used and licensed by or for the Government for governmental purposes without the payment of any royalties to us on the invention.

BACKGROUND OF THE INVENTION

Infrared polarimetry is a technique for acquiring and processing emissive and scattered radiation in the infrared bands and, as such, has applications in astronomy, space exploration, materials characterization, plasma diagnostics, biological measurements and characterization of military targets. In the military, exemplar applications of polarization information occur in enhancement of the discrimination of targets from clutter and enhancement of feature identification. These enhancements reduce false alarm rates in both human and automatic target recognition and enable improvements in target classification, counter-measure rejection and defeat of camouflage.

However, infrared polarimetry is still in a rather immature state of development. Hence it is not used in any existing or planned military system, even though some research has indicated that infrared polarization imagery can provide surface orientation information, distinction between flat plates and cylinders and discrimination between tanks and heated flat plate decoys, all based on differences in polarization signatures of the various items. It has been discovered further that polarization imagery is possible with relatively cool objects.

Much of the difficulties encountered both in military and peaceful applications of the nascent infrared polarimetry are due to significant limitations in the extant instrumentation. One such limitation is the polarization aberrations introduced by the instrument itself. In addition, optical components of the instruments introduce some change in the polarization state of the infrared radiation as the radiation propagates through the instrument. Optical coatings, scattering and birefringence effects also may cause unintended changes in the polarization state that perturb the intended polarization changes wrought about by the polarizers and retarders.

SUMMARY OF THE INVENTION

The polarization-resolving infrared imager for filtering and processing polarized infrared radiation as described in detail hereinbelow utilizes the detector configurations of either a first-generation infrared imaging detector device having 60 (rows)×1 (column) of detector elements (pixels) or a second-generation infrared imaging detector device having at least 240 (rows)×4 (columns) of detector elements (pixels).

In the embodiment using a first-generation infrared imaging detector device, prior to being incident on the detector device, the incoming infrared radiation impinges on a polarization filter that is stepped through three polarization positions (e.g. 0, 45 and 90 degrees) to separate the radiation into portions that are, respectively, at 0, 45 and 90 degrees of polarized radiation. The polarization filter, which is physically separate from the detector device, transmits the three portions of polarized radiation to be detected by the detector device and processed by suitable video electronics to produce various image combinations.

In the embodiment using a second-generation infrared imaging detector device which is the preferred embodiment of the invention, polarization-filtering wire grids are integrated onto the detector elements. Three of the four detector elements in each row of the second-generation infrared imaging detector device have coupled thereto polarization elements to filter or select radiation portions of horizontal polarization, vertical polarization and 45-degree polarization, respectively. The fourth detector element in the row remains clear to detect the total infrared radiation with no polarization distinction. This pattern of selecting the three polarization orientations is repeated at each succeeding row of detector elements. Using a scan mirror of sufficient sweep in conjunction with the detector device and the polarization-filtering grid results in one frame of the scene representing horizontal polarization, one frame representing vertical polarization and one frame representing 45-degree polarization, all with one sweep of the scan mirror in real-time scenario. This provides near simultaneous infrared scene information at different polarizations.

DESCRIPTION OF THE DRAWING

FIG. 5 illustrates the alignment of the detector elements with the polarization-filtering elements in the preferred embodiment.

DESCRIPTION OF THE PREFERRED EMBODIMENT

Figure 1:
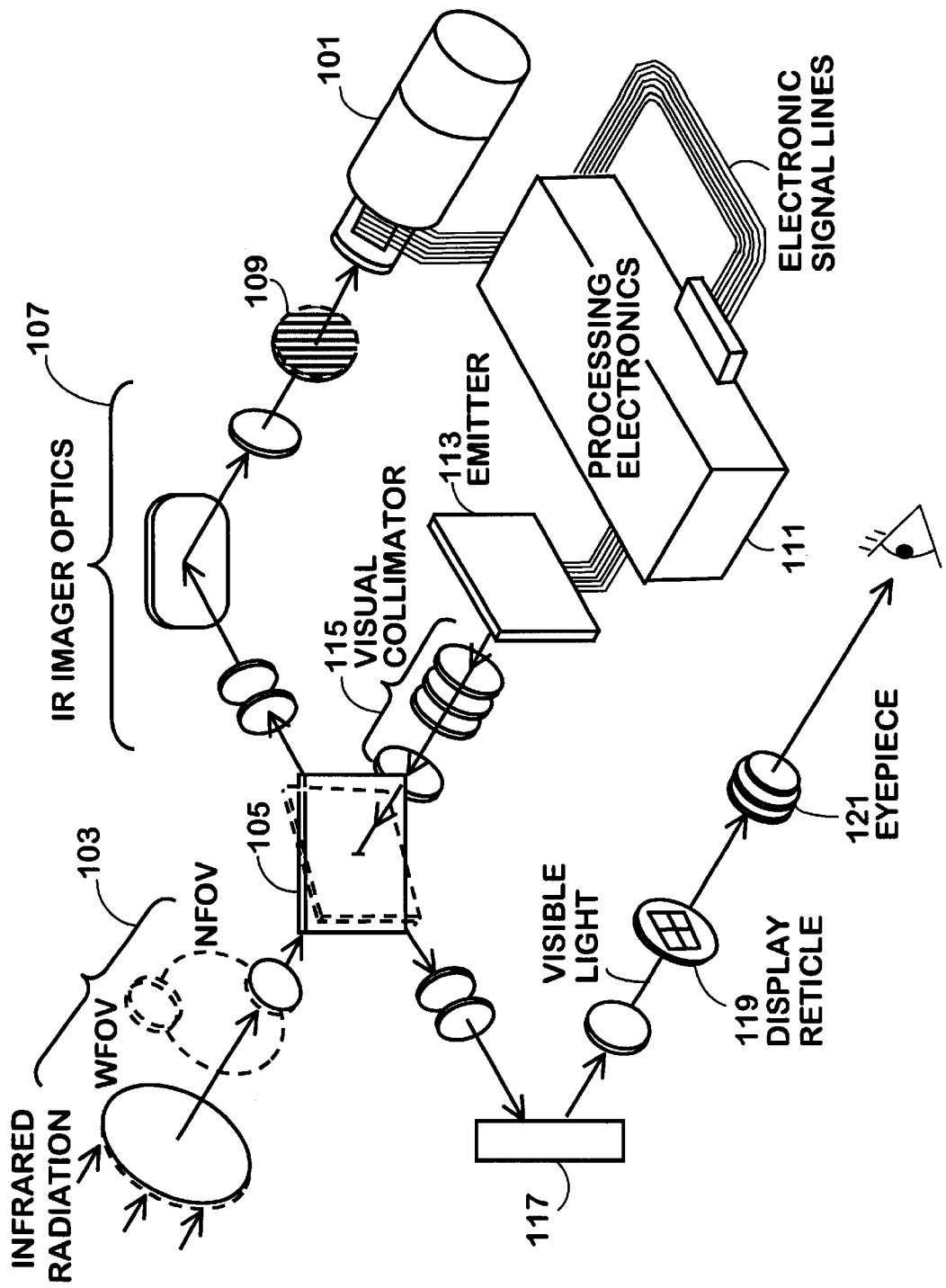
FIG. 1 is a diagram of an embodiment of the invention that uses a first-generation forward-looking infrared detector device and a rotating polarization filter.
Figure 2:
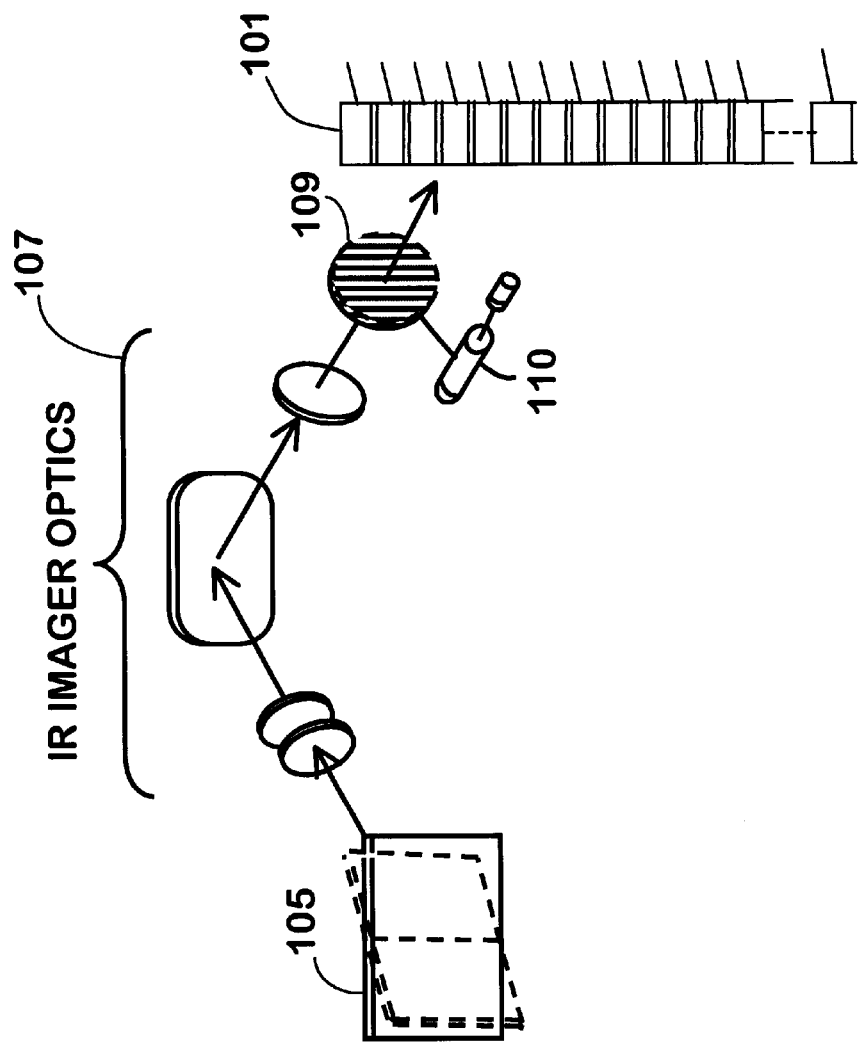
FIG. 2 illustrates rotating polarization filter 109 and stepper motor 110 coupled to drive the filter.

Referring now to the drawing wherein like numbers represent like parts in each of the several figures and solid lines with arrow heads indicate beam paths (except otherwise stated in the drawing), FIG. 1 depicts one embodiment of the invention that uses a rotating or stepped-through polarization filter 109 with a first-generation forward-looking infrared (FLIR) imaging detector device 101 which is comprised of 60 rows of single detector elements. The FLIR imaging detector device, in general, is an electro-optical system that incorporates both visible and infrared optics and is capable of rendering an infrared (IR) scene in a visible format. The embodiment depicted in FIG. 1 takes advantage of the configuration of prior art FLIR imaging system that produces infrared images with no polarization distinction and improves the system by providing a means for separating the incoming infrared radiation into portions of differing polarizations so that different aspects of the imaged scene can be observed and characterized. In operation of the improved system, first-generation FLIR detector device 101 detects incident IR radiation that is first collected and focussed by optical assembly 103 made up of wide-field-of-view and narrow-field-of-view lenses. The optical assembly then forwards the IR radiation to tiltable scan mirror 105 having a pre-set tilt pattern and a pre-set scan pattern that consists of a forward scan and a reverse (interlace) scan. Thence the IR radiation proceeds to IR imager optics 107 which directs the IR radiation beam further to rotatable linear polarization filter 109. Linear polarization filter 109 consists of a wire grid of polarization elements with line width and spacing much less than the wavelength of the incoming radiation. Polarization filter 109 is coupled to and actuated by stepper motor 110, as illustrated in FIG. 2, which is in synchrony with scanning mirror 105 such that after the mirror completes a forward scan and a reverse scan that make up one complete scan cycle, the motor rotates the filter in 45-degree increments where it is held in place at each position for a given duration of time. In this fashion, polarization filter 109 steps through three polarization positions (e.g. 0, 45 and 90 degrees) with each position remaining in place for a sufficient length of time to allow the scene to be scanned twice (once forward and once reverse) over FLIR detector device 101 to generate an interlaced image. As polarization filter 109 steps through the polarization positions, the various positions of the filter come into field of view in successive sequence and the positions with horizontal polarization passes through only that portion of the IR radiation which is horizontally polarized while the positions with vertical polarization and 45-degree polarization send forward only those portions which are vertically polarized and 45-degree polarized, respectively. FLIR detector device 101, also in sequence, collects radiation of these three polarizations, each detector element receiving the appropriate (0, 45 or 90 degrees) polarized radiation during the two interlaced scans making up one complete scan cycle that is necessary to generate an image frame. As a result of above-described operation, three polarized image frames are obtained instead of one frame of total undifferentiated infrared radiation. FLIR detector device 101 and processing electronics 111 then convert the three developed polarized image frames and the undifferentiated image frame into electrical signals which are utilized to generate various image combinations representing the degree of polarization, total radiation, object orientation and other image differences within the scanned scene. The selected processed image frame within the video electronics 111 is used to drive emitter 113 to produce a visible image. Subsequently visual collimator 115 collimates the visible image and transmits it onto the back side of scan mirror 105 which, being reflective, reflects the image to roof mirror 117. From the roof mirror, the visible image is steered onto display reticle 119 for viewing through eyepiece 121.

A significant drawback of the above-described embodiment of using a rotating polarization filter is that the information concerning the various polarization orientations of incoming IR radiation (descriptive of a given scene) is not collected simultaneously and the scene may change while the polarization filter is being rotated (typically a detector frame time), thereby causing the loss of one frame of data. Further, the rotation itself may introduce beam steering and spurious modulations in the detector array response and interlaced images may contain polarization error in high gradient conditions.

Figure 3:
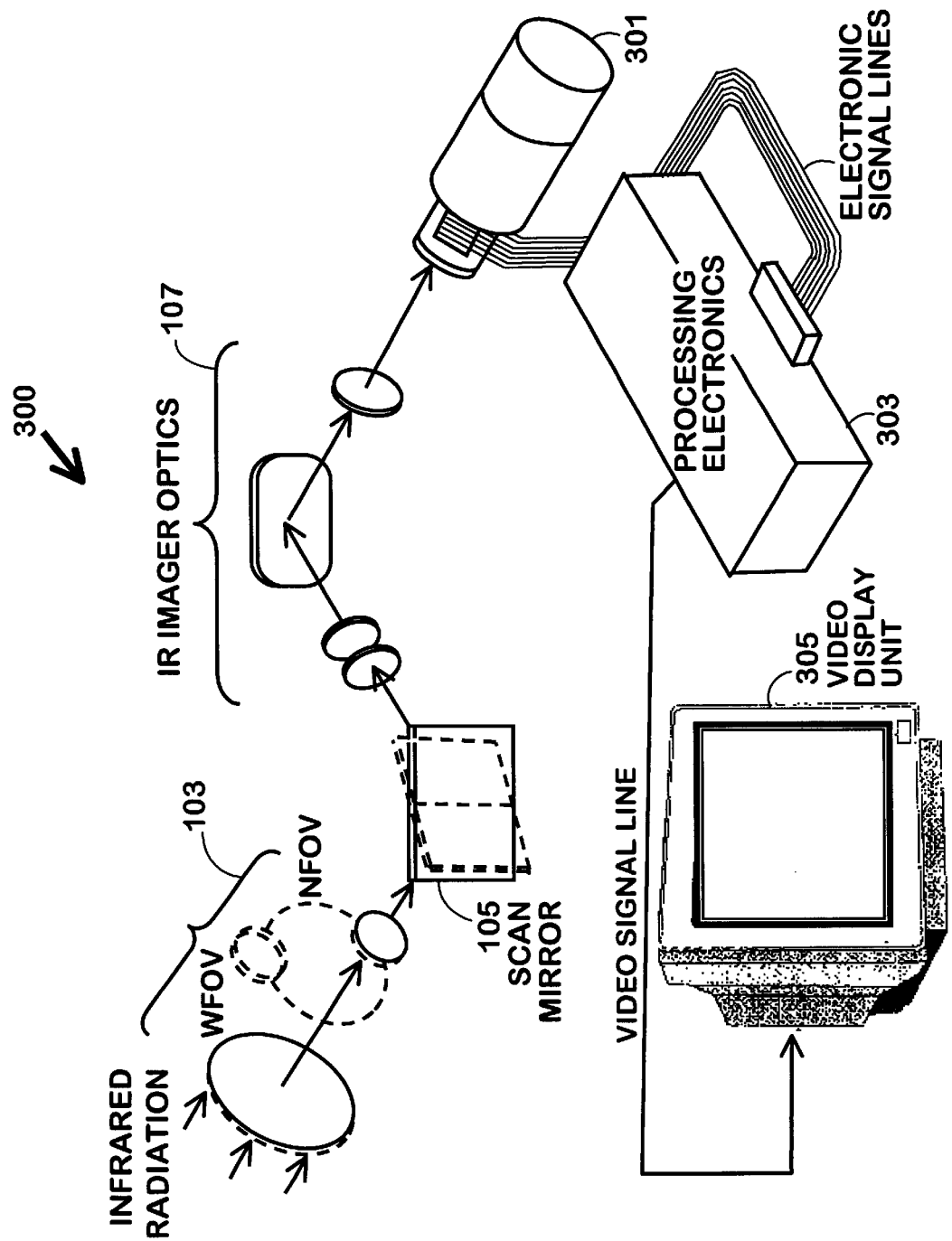
FIG. 3 depicts a preferred embodiment of polarization-resolving infrared imager.
Figure 4:
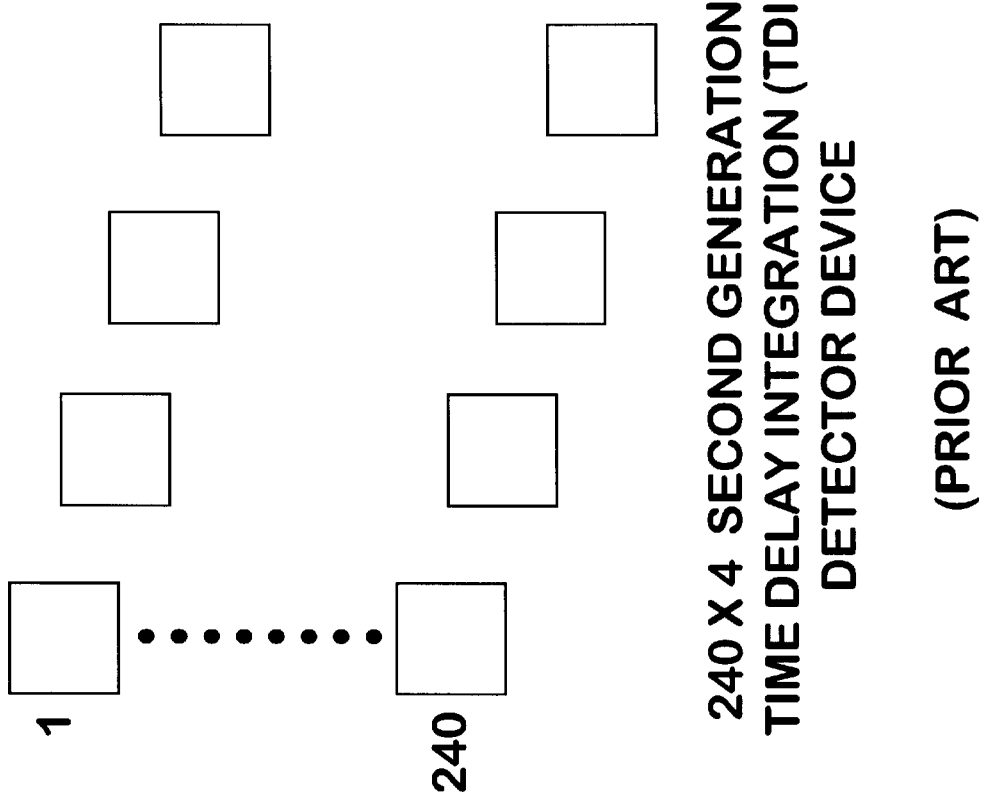
FIG. 4 is a diagram of the configuration of extant second-generation infrared imaging detector device.

These limitations are largely removed by the preferred embodiment of the polarization-resolving infrared imager 300 as depicted in FIG. 3. In the preferred embodiment, imager 300 collects the incoming IR radiation in a manner similar to that of the embodiment shown in FIG. 1 but utilizes a second-generation FLIR detector device 301. The second-generation FLIR detector device 301 contains a larger detector array comprised of at least 240 horizontal rows by 4 vertical columns of detector elements, thus affording greater resolution and sensitivity.

Polarization selecting (or filtering) of the IR radiation beam before the beam is incident on the detector elements is achieved by a polarization grid that is structurally integrated into the detector elements which integration, in effect, produces detector-polarization combination units. For best result, the polarization grid is fabricated in the manner described in U.S. Pat. No. 4,946,231 (Aug. 7, 1990; Helmut H. Pistor, the inventor and the United States Department of the Army, the assignee) whose teaching is incorporated herein in its entirety. Using the photographic process taught by Pistor, one may produce a grid of plural polarization elements 501 with a spacing much less than the wavelengths of the incoming radiation. A polarization grid thusly made is utilized in the transmissive mode. It is affixed to the detector elements of second-generation FLIR detector device 301 such that the detector elements of any one of the first three vertical columns have coupled thereto identical polarization elements while each column has paired therewith polarization elements that are of differing polarization orientation from those of the other two columns of a set of four adjacent columns: for example, the first column has vertical polarization elements to filter therethrough only the portion of incoming radiation that is vertically polarized, the second column has horizontal polarization elements to filter through only horizontally polarized portion and the third column has 45-degree polarization elements to pass therethrough the 45-degree polarized portion while the fourth column does not have polarization elements so that the total radiation can pass through with no polarization distinction. FIG. 5 illustrates this alignment of the detector elements with the polarization elements and shows the column of unfiltered detector elements.

With a suitable scan mirror 105 scanning the focussed incoming IR radiation through the total field of view, detector 301, now having polarization elements integrated thereto, performs near simultaneous detections of infrared scenes at different polarizations. This, in turn, provides precise registration of the different polarizations while making it possible to process simultaneously the different polarizations of incoming IR radiation on a real-time basis. Processing electronics 303 receives the electrical signals from second-generation FLIR detector device 301 and produces corresponding video signals which are transmitted to video display unit 305 for display.

The polarization-resolving infrared imager digitizes each polarization image along with the unfiltered image and may process and display them in a variety of ways. For example, any one of the three polarization images may be processed and displayed with respect to each other or with respect to the normal unfiltered image.

Although a particular embodiment and form of this invention has been illustrated, it is apparent that various modifications and embodiments of the invention may be made by those skilled in the art without departing from the scope and spirit of the foregoing disclosure. Accordingly, the scope of the invention should be limited only by the claims appended hereto.

We claim:

1. In a system for detecting and processing incoming infrared radiation to output visible images therefrom, the system having an optical assembly for gathering and focussing the infrared radiation incident thereon, a tiltable scan mirror having a pre-set scan pattern and a means for directing the infrared radiation in a pre-determined direction, AN IMPROVEMENT for separating the different polarizations of the incoming infrared radiation descriptive of a pre-selected scene so that various aspects of the pre-selected scene can be differentiated, said IMPROVEMENT comprising: a first-generation forward-looking infrared detector device comprised of 60×1 detector elements, said detector device being positioned to receive the infrared radiation from the directing means and convert the infrared radiation into electrical signals; a rotatably-mounted polarization filter, said filter being adapted for detecting and separating incident infrared radiation into portions of different polarizations, said filter further being positioned between said directing means and said first-generation detector device so as to receive infrared radiation from said directing means and separate the infrared radiation into portions having different polarizations and subsequently transmitting said portions of infrared radiation to said first-generation detector device; a means for rotating said polarization filter; and a means for processing and displaying the electrical signals as visible imagery, said processing and displaying means being coupled to said first-generation detector device.

2. In a system for detecting and processing incoming infrared radiation to output visible images therefrom, AN IMPROVEMENT for differentiating various aspects of a pre-selected scene as set forth in claim 1, wherein said rotating means is a stepper motor, said motor being synchronized with the scan pattern of the scan mirror such that said rotating means moves said polarization filter by a pre-determined angle increment in a pre-determined direction with each successive scan cycle of the scan mirror.

3. In a system for detecting and processing incoming infrared radiation to output visible images, AN IMPROVEMENT for differentiating various aspects of a pre-selected scene as set forth in claim 2, wherein said pre-determined rotation angle increment of said polarization filter is 45 degrees, thereby enabling said filter, on successive rotations, to separate incident infrared radiation into portions having polarization orientations of 0, 45 and 90 degrees, respectively.

4. In a system for detecting and processing incoming infrared radiation to output visible images, AN IMPROVEMENT as set forth in claim 3, wherein after each rotation, said filter remains in position for a sufficient duration to allow one complete scan cycle of the scan mirror.

5. A polarization-resolving infrared imager for detecting and processing infrared radiation to output visible images that have polarization differentiation, said imager comprising: an optical assembly for gathering and focussing infrared radiation incident thereon; a detector for detecting said infrared radiation; a means for separating said infrared radiation into several portions, each portion having a different polarization orientation, said separating means being positioned between said optical assembly and said detector and further being coupled to said detector; a means for directing said infrared radiation from said optical assembly to said detector; and a means for processing and displaying said focussed, polarization-separated infrared radiation as a visible image.

6. A polarization-resolving infrared imager for detecting and processing infrared radiation as set forth in claim 5, wherein said detector is a second-generation forward-looking infrared detector device comprising an array of at least 240 rows by 4 columns of detector elements, said detector being adapted for converting detected infrared radiation into electrical signals.

7. A polarization-resolving infrared imager as set forth in claim 6, wherein said polarization separating means comprises a grid array of at least 240 rows by 4 columns of polarization filtering elements, said filtering elements being integrated into said detector such that there is a one-to-one correspondence between said detector elements and said polarization filtering elements.

8. A polarization-resolving infrared imager as set forth in claim 7, wherein said directing means comprises a reflector; a scan mirror positioned to scan said infrared radiation being gathered and focussed by said optical assembly and transmit said scanned radiation to said reflector from whence to be further reflected toward said detector, said scan mirror having a sweep sufficiently wide to irradiate said 4 columns of said detector at any of said rows with one sweep of said mirror through the total field of view.

9. A polarization-resolving infrared imager as set forth in claim 8, wherein said 4 columns of polarization filtering elements transmit therethrough, respectively, horizontal, vertical, 45-degree polarizations and total undifferentiated incident infrared radiation so that one sweep of said scan mirror provides one frame of any given scene in each of said polarizations and one frame with no polarization distinction.

10. A polarization-resolving infrared imager as set forth in claim 9, wherein said processing and displaying means comprises processing electronics coupled to receive said electrical signals from said detector and convert said electrical signals to corresponding video signals and a video display unit coupled to said processing electronics to receive therefrom and display said video signals.

11. In a system for detecting and processing infrared radiation, the system having an optical assembly for gathering and focussing infrared radiation incident thereon and a means for directing the infrared radiation in a pre-determined direction, AN IMPROVEMENT for obtaining three different polarizations of a pre-selected scene on a real-time basis, said IMPROVEMENT comprising: a second-generation forward-looking infrared detector comprised of at least 240×4 detector elements, said detector being positioned to receive the infrared radiation from the directing means and convert the infrared radiation into electrical signals; a plurality of polarization filtering elements for filtering horizontal, vertical and 45-degree polarizations of a pre-selected scene, said polarization filtering elements being coupled to said detector elements on a one-to-one correspondence; and a means for processing and displaying the electrical signals as visible imagery.

* * * * *